(12) United States Patent
Singla

(10) Patent No.: US 11,911,054 B2
(45) Date of Patent: Feb. 27, 2024

(54) NEUROASPIRATION CATHETER FOR THROMBECTOMY

(71) Applicant: Rutgers, the State University of New Jersey, New Brunswick, NJ (US)

(72) Inventor: Amit Singla, New Brunswick, NJ (US)

(73) Assignee: RUTGERS, THE STATE UNIVERSITY OF NEW JERSEY, New Brunswick, NJ (US)

(*) Notice: Subject to any disclaimer, the term of this patent is extended or adjusted under 35 U.S.C. 154(b) by 0 days.

(21) Appl. No.: 18/125,064

(22) Filed: Mar. 22, 2023

(65) Prior Publication Data
US 2023/0301671 A1   Sep. 28, 2023

Related U.S. Application Data

(60) Provisional application No. 63/322,288, filed on Mar. 22, 2022.

(51) Int. Cl.
  *A61B 17/22* (2006.01)
  *A61M 25/00* (2006.01)
  *A61M 25/01* (2006.01)

(52) U.S. Cl.
  CPC .... *A61B 17/22* (2013.01); *A61B 2017/22044* (2013.01); *A61B 2217/005* (2013.01); *A61M 25/0071* (2013.01); *A61M 2025/0042* (2013.01); *A61M 2025/0079* (2013.01); *A61M 2025/0177* (2013.01); *A61M 2025/0183* (2013.01)

(58) Field of Classification Search
CPC .............. A61M 2025/0177; A61M 2025/0183
See application file for complete search history.

(56) References Cited

U.S. PATENT DOCUMENTS

| | | | | |
|---|---|---|---|---|
| 4,928,693 A | * | 5/1990 | Goodin | A61B 5/0215 600/487 |
| 5,197,949 A | * | 3/1993 | Angsupanich | A61M 1/774 604/35 |
| 5,443,457 A | | 8/1995 | Ginn et al. | |
| 5,855,546 A | | 1/1999 | Hastings et al. | |
| 5,972,013 A | * | 10/1999 | Schmidt | A61B 17/3468 604/164.01 |
| 6,056,719 A | * | 5/2000 | Mickley | A61M 25/104 604/96.01 |

(Continued)

OTHER PUBLICATIONS

Patent Cooperation Treaty, International Search Report and Written Opinion for PCT/US2023/015973, 10 pages, dated Jul. 6, 2023.

(Continued)

*Primary Examiner* — Adam Marcetich
(74) *Attorney, Agent, or Firm* — Viksnins Harris Padys Malen LLP

(57) ABSTRACT

Described herein is a neuroaspiration catheter for removing a blood clot in a blood vessel. The neuroaspiration catheter includes a first tube, a second tube and a wire for guiding the navigation of the catheter. The wire can be navigated to the site of the blood clot, aid the navigation of the catheter, and left in the blood vessel during and after the aspiration. If the aspiration fails, the catheter can be quickly navigated back to the site of the blood clot using the wire as a guide. Also described herein is a method of removing a blood clot using the neuroaspiration catheter.

20 Claims, 2 Drawing Sheets

(56) References Cited

U.S. PATENT DOCUMENTS

| | | | |
|---|---|---|---|
| 6,099,454 A | 8/2000 | Hastings et al. | |
| 6,159,195 A | 12/2000 | Ha et al. | |
| 6,494,846 B1* | 12/2002 | Margolis | A61M 25/104 600/585 |
| 7,294,117 B2 | 11/2007 | Provost-Tine et al. | |
| 8,021,351 B2 | 9/2011 | Boldenow et al. | |
| 8,206,370 B2 | 6/2012 | Von et al. | |
| 8,252,015 B2 | 8/2012 | Leeflang et al. | |
| 8,758,325 B2 | 6/2014 | Webster et al. | |
| 10,188,409 B2 | 1/2019 | Smalling | |
| 10,426,497 B2 | 10/2019 | Chou et al. | |
| 2004/0039369 A1* | 2/2004 | Shelso | A61M 25/005 604/524 |
| 2004/0049225 A1* | 3/2004 | Denison | A61F 2/013 606/200 |
| 2004/0106866 A1* | 6/2004 | Ookubo | A61M 25/0068 600/437 |
| 2004/0204629 A1* | 10/2004 | Knapp | A61B 17/0218 600/156 |
| 2005/0015073 A1* | 1/2005 | Kataishi | A61B 17/22 604/528 |
| 2005/0197669 A1* | 9/2005 | Fisher | A61M 25/005 604/103.04 |
| 2005/0240165 A1* | 10/2005 | Miki | A61M 25/0068 604/528 |
| 2006/0041246 A1* | 2/2006 | Provost-tine | A61M 25/0043 604/528 |
| 2006/0189921 A1 | 8/2006 | Galdonik et al. | |
| 2007/0060911 A1 | 3/2007 | Webster et al. | |
| 2007/0191812 A1* | 8/2007 | Nishide | A61M 25/0102 604/523 |
| 2007/0293846 A1 | 12/2007 | Von et al. | |
| 2008/0077085 A1* | 3/2008 | Eidenschink | A61M 25/0028 604/164.01 |
| 2009/0270800 A1* | 10/2009 | Spurchise | A61M 25/0074 604/95.04 |
| 2009/0270801 A1* | 10/2009 | Shimada | A61M 25/0029 604/533 |
| 2010/0305678 A1* | 12/2010 | Alaswad | A61M 25/09 604/101.03 |
| 2011/0112564 A1* | 5/2011 | Wolf | A61M 25/0074 606/159 |
| 2011/0160834 A1* | 6/2011 | Aggerholm | A61F 2/958 604/528 |
| 2012/0016344 A1 | 1/2012 | Kusakabe | |
| 2012/0071838 A1 | 3/2012 | Fojtik | |
| 2012/0185030 A1* | 7/2012 | Igaki | A61F 2/958 623/1.11 |
| 2013/0053828 A1* | 2/2013 | Hensler | A61M 1/76 15/415.1 |
| 2013/0131615 A1* | 5/2013 | Riordan | A61M 1/84 604/319 |
| 2014/0309533 A1* | 10/2014 | Yamashita | A61M 25/0009 600/463 |
| 2015/0112307 A1 | 4/2015 | Margolis | |
| 2015/0133800 A1* | 5/2015 | McCaffrey | A61M 25/007 600/486 |
| 2015/0217084 A1* | 8/2015 | Tassoni, Jr. | A61L 29/04 29/428 |
| 2016/0106446 A1* | 4/2016 | Welch | A61L 29/041 606/127 |
| 2016/0250397 A1 | 9/2016 | Griffin et al. | |
| 2016/0302762 A1* | 10/2016 | Stigall | A61B 5/0066 |
| 2017/0290598 A1* | 10/2017 | Culbert | A61M 25/0026 |
| 2017/0333237 A1 | 11/2017 | Walzman | |
| 2018/0028205 A1 | 2/2018 | Chou et al. | |
| 2018/0200484 A1* | 7/2018 | Haldis | A61M 25/0169 |
| 2018/0296233 A1 | 10/2018 | Schwager | |
| 2018/0338770 A1 | 11/2018 | Mogi et al. | |
| 2021/0228844 A1 | 7/2021 | Ogle | |
| 2021/0298775 A1 | 9/2021 | Nguyen et al. | |
| 2023/0066121 A1* | 3/2023 | Dolan | A61B 17/320708 |

OTHER PUBLICATIONS

Teleflex, "Teleflex. Twin-Pass® Dual Access Catheters", https://teleflex.com/USA/en/product-areas/interventional/coronary-interventions/twin-pass-dual-access-catheters/index.html, 6 pages (2021).

Nikoubashman, O, et al., "Necessary Catheter Diameters for Mechanical Thrombectomy with ADAPT", AJNR Am J Neuroradiol 38, 2277-2281 (2017).

* cited by examiner

NEUROASPIRATION CATHETER FOR THROMBECTOMY

CROSS-REFERENCE TO RELATED APPLICATIONS

This application claims priority to U.S. Provisional Application No. 63/322,288, filed Mar. 22, 2022, the contents of which are hereby incorporated by reference herein.

BACKGROUND

Thrombus, the blood clot in blood vessels, blocks blood flow in blood vessels and causes serious conditions such as, but not limited to, stroke, heart attack, and/or necrosis in the other organs. Catheters are used to treat the occlusion of the blood vessels by aspirating out the blood clot from the blood vessels and/or removing the blood clot using stent-retriever in addition to aspiration. Navigating catheters to the site of the blood clot; however, is not an easy task and sometimes repeated attempts are made which are time consuming and can sometimes result in aborted procedures. Aborted procedures can result in more damage to the brain, heart or other organ due to unsuccessful opening up of the blood vessel.

Therefore, there is a need for improved catheter designs that can simplify the navigation process through blood vessels and/or facilitate clot removal. The present invention addresses this need.

BRIEF DESCRIPTION OF THE DRAWINGS

The following detailed description of exemplary embodiments will be better understood when read in conjunction with the appended drawings. For the purpose of illustrating, non-limiting embodiments are shown in the drawings. It should be understood, however, that the instant specification is not limited to the precise arrangements and instrumentalities of the embodiments shown in the drawings.

DETAILED DESCRIPTION

Figure 1:
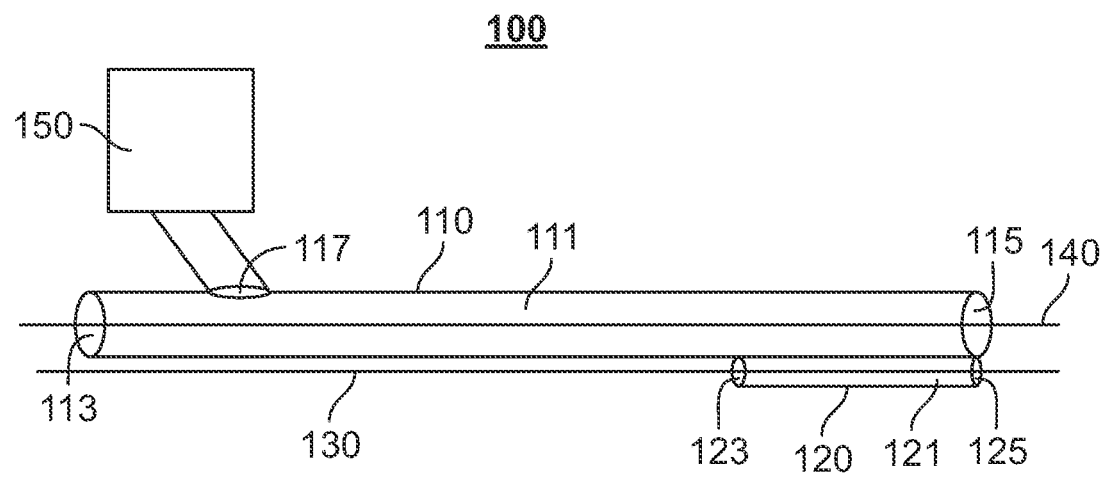
FIG. 1 is a side view illustration of a neuroaspiration catheter in accordance with some embodiments.

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Conventionally, the procedures for catheter-based removal of blood clots from the brain use several catheters. For example, the surgeon will access the carotid or vertebral artery with a diagnostic catheter. Once the diagnostic catheter has been navigated to the carotid or vertebral artery, the surgeons then ride a guide catheter over the diagnostic catheter until the guide catheter reaches the target vessel of interest. The diagnostic catheter is then removed, leaving only the guide catheter in place. The surgeon will then advance an aspiration catheter (also referred to herein as a "neuroaspiration catheter") over a microwire and a microcatheter inside the guide catheter and navigate the microwire and microcatheter across the blood clot in, for example, the middle cerebral artery or distal internal carotid artery to the second segment of the middle cerebral artery beyond the bifurcation. Typically, the surgeon will navigate the microwire across the blood clot first, followed by the microcatheter in, for example, the middle cerebral artery across the bifurcation. The surgeon will then advance the aspiration catheter over the microwire and microcatheter until reaching the face of the thrombus. The surgeons remove the microwire and microcatheter, leaving only the aspiration catheter in place, which is then used to aspirate out the thrombus.

Alternatively, surgeons sometimes use a stent-retriever along with aspiration to engage the clot. When a stent-retriever is used, after removing the microwire, the stent-retriever is passed through the microcatheter across the clot. Then the microcatheter is removed leaving the stent-retriever integrating the thrombus within itself in place along with the aspiration catheter at the face of the thrombus. The aspiration catheter is then pulled along with the stent-retriever.

The removal of the blood clot and revascularization, however; is not always achieved in the first try and the procedures described sometimes need to be repeated several times before the blood clot can be removed. Further, the procedures sometimes fail ultimately, and the clot is not successfully removed.

One issue with the conventional method is that the microwire and the microcatheter need to be removed for the aspiration to take place. Thus, if the aspiration fails to remove the blood clot and the navigation of the aspiration catheter needs to be done again, re-navigation of the microwire and the microcatheter must be performed. The navigation of the microwire and the microcatheter (such as in the middle cerebral artery and the internal carotid artery) can require a substantial amount of time and is not always successful. Since brain cells will continue to die and brain tissues will continue to be damaged unless the blood supply is restored quickly, the additional time required to re-navigate the microwire and the microcatheter can result in larger strokes in the patients.

To address the above observed shortcomings in the conventional procedures, a novel aspiration catheter is designed and described herein.

Definitions

As used herein, each of the following terms has the meaning associated with it in this section. Unless defined otherwise, all technical and scientific terms used herein generally have the same meaning as commonly understood by one of ordinary skill in the art to which this disclosure belongs. Generally, the nomenclature used herein and the laboratory procedures in animal pharmacology, pharmaceutical science, peptide chemistry, and organic chemistry are those well-known and commonly employed in the art. It should be understood that the order of steps or order for performing certain actions is immaterial, so long as the present teachings remain operable. Any use of section headings is intended to aid reading of the document and is not to be interpreted as limiting; information that is relevant to a section heading may occur within or outside of that particular section. All publications, patents, and patent documents referred to in this document are incorporated by reference herein in their entirety, as though individually incorporated by reference.

In the application, where an element or component is said to be included in and/or selected from a list of recited elements or components, it should be understood that the element or component can be any one of the recited elements or components and can be selected from a group consisting of two or more of the recited elements or components.

In the methods described herein, the acts can be carried out in any order, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

In this document, the terms "a," "an," or "the" are used to include one or more than one unless the context clearly dictates otherwise. The term "or" is used to refer to a nonexclusive "or" unless otherwise indicated. The statement "at least one of A and B" or "at least one of A or B" has the same meaning as "A, B, or A and B."

"About" as used herein when referring to a measurable value such as an amount, a temporal duration, and the like, is meant to encompass variations of ±20% or ±10%, in certain embodiments ±5%, in certain embodiments ±1%, in certain embodiments ±0.1% from the specified value, as such variations are appropriate to perform the disclosed methods.

Nueroaspiration Catheter

In some aspects, the present invention is directed to a neuroaspiration catheter.

Figure 2:
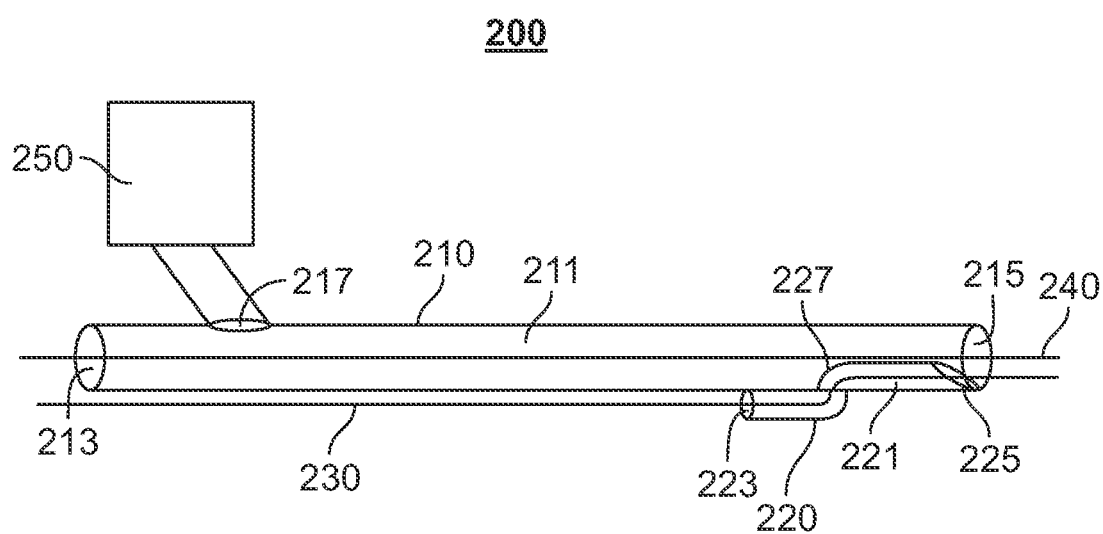
FIG. 2 is a side view illustration of a neuroaspiration catheter in accordance with some embodiments.

FIGS. 1 and 2 described two non-limiting embodiments of the catheter. It is worth noting that individual elements shown in FIGS. 1 and 2 do not have to be combined with other elements of the same figure. One of ordinary skill in the art would understand that these elements can be combined with other elements shown in the other figure, or elements not shown in the figures.

Referring to FIG. 1, in some embodiments, the catheter 100 includes a first tube 110 having a first lumen 111, a first opening 113, and a second opening 115 for aspiration; a second tube 120 having a second lumen 121, a first opening 123 proximal to the second opening 115 of the first tube 110, and a second opening 125 proximal to or at the level of the second opening 115 of the first tube 110, wherein the second tube 120 is integrally formed with and substantially parallel to the first tube 110; and a wire 130 movable inside the second lumen 121.

In some embodiments, only a short section of the wire (such as 25 cm or less) is inside the second tube. In some embodiments, the rest of the wire 130 is exposed as shown in FIG. 1. In some embodiments, the portions of the wire 230 that are not inside the second tube 220 are either exposed or directly inside the first lumen 211, as shown in FIG. 2. Such partially exposed wire is sometimes referred to as a "rapid exchange wire" herein.

In some embodiments, the wire 130 is a microwire or a guide wire. The wire 130, as well as the second tube 120 in which the wire 130 moves, is configured such that the wire can be navigated to the blood clot site, moved past the blood clot, and left there as further guidance for navigating the aspiration catheter back in the event that the catheter fails to remove the blood clot in the first or the first several attempts. The configuration of the wire 130 and the second tube 120 include the shape and dimensions of the elements, which are described elsewhere herein.

In some embodiments, the second opening 125 of the second tube 120 is substantially at the same level as the second opening 115 of the second tube 110. When the two openings (125 and 115) are substantially at the same level, the contacting point between the wire 130 the second opening 125 is close to the leading edge of the first tube and therefore the leading edge of the main body of the catheter. As such, the wire 130 is able to better guide the navigation of the catheter.

In some embodiments, the first opening 113 of the first tube 110 is for connecting to a suction device and/or advancing another guidewire if needed for additional support to advance the aspiration catheter or as a channel to advance the microcatheter if needed to use the stent-retriever. In some embodiments, the first tube 110 has a third opening 117 proximal to the second opening 115, which is for connecting to a suction device.

In some embodiments, the second tube 120 is integrally formed with the first tube 110 at a portion thereof proximal to the second opening 115 of the first tube 110.

In some embodiments, the length of the second tube ranges from about 5 cm to about 40 cm, such as about 7.5 cm to about 30 cm, about 10 cm to about 25 cm, or about 12.5 cm to about 20 cm.

In some embodiments, the second opening 125 of the second tube 120 is outside the first lumen 111. Alternatively, referring to FIG. 2, the second opening 225 of the second tube 220 is inside the first lumen 211. When the second opening of the second tube is outside the first lumen, the construction of the catheter is simpler and the friction between the second tube 120 and the wire 130 is smaller. When the second opening of the second tube is inside the first lumen, the advancing movements of the catheter inside blood vessels is easier as there is less friction between the catheter and the blood vessel walls, and the navigation of the catheter is easier.

Referring to FIG. 1, in some embodiments, the first opening 123 of the second tube 120 is outside the lumen 111 of the first tube. If the first opening 123 is outside the lumen 111 of the first tube, the wire 130 does not have to extend across the first opening 113 of the first tube 110, and would not interfere with the suction force applied to either the first opening 113 or the third opening 117.

Figure 3:
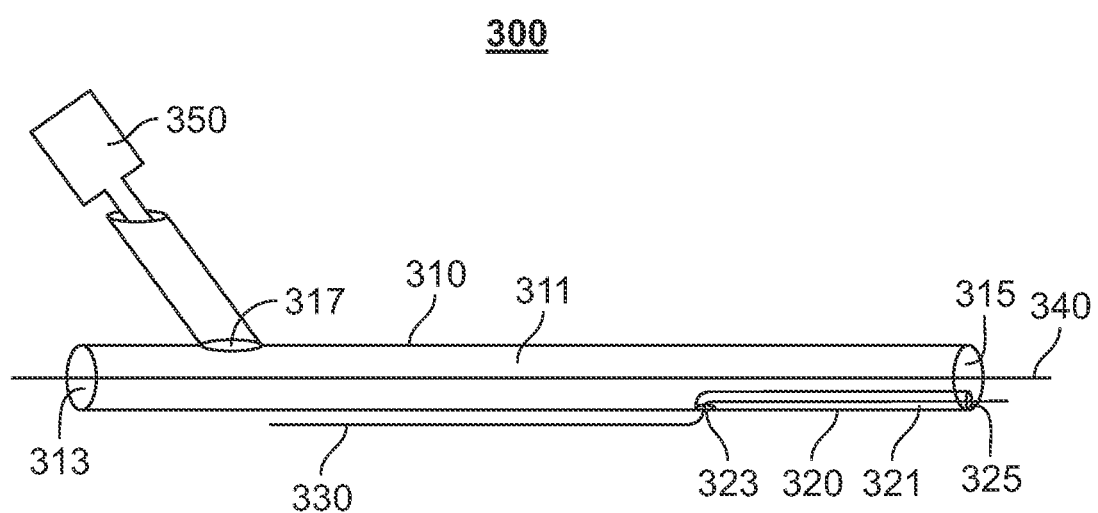
FIG. 3 is a side view illustration of a neuroaspiration catheter in accordance with some embodiments.

Referring to FIG. 3, in some embodiments, the first opening 323 of the second tube 320 is on the wall of the first tube 310 and the second opening 325 is inside the second lumen 311. According to these embodiments, the catheter 300 is compact. Furthermore, the friction between the catheter and the blood vessel walls during the advancing movements of the catheter can be reduced, and the friction between the wire 330 and the second tube 320 is not excessively large.

Referring to FIG. 2, in some embodiments, the diameter of the second lumen 221 and the diameter of the wire 230 are matched such that the first opening 223 of the second tube 220 and the second opening 225 of the second tube 220 are not substantially in fluid communication. When suction force is applied to either the first opening 213 or the third opening 217 of the first tube, the lumen 211 has a negative pressure. The precise matching of the two diameters that substantially block the fluid communication would block the flow from the first opening 223 to the second opening 225 via the second lumen 221, thereby maintaining the negative pressure in the first lumen 211, which is required for aspirating the blood clot.

In some embodiments, the diameter of the first lumen is about twice or larger than the diameter of the second lumen, such as about three times or larger, or four times or larger.

In some embodiments the diameter of the first tube 110 at a location proximal to the second opening 115 thereof ranges from about 1.40 mm to about 2.2 mm, such as about 1.60 mm to about 2.10 mm, or about 1.80 mm to about 2.00 mm.

In some embodiments, the diameter of the first lumen 111 ranges from about 1.30 mm to about 2.30 mm, such as about 1.50 mm to about 2.20 mm, or about 1.70 mm to about 2.10 mm.

In some embodiments, the diameter of the second lumen 121 ranges from about 0.25 mm to about 0.60 mm, such as about 0.25 mm to about 0.50 mm, or about 0.30 mm to about 0.40 mm.

In some embodiments, the diameter of the wire 130 ranges from about 0.20 mm to about 0.55 mm, such as about 0.15 mm to about 0.50 mm, about 0.20 mm to about 0.50 mm, or about 0.3 mm to about 0.4 mm.

In some embodiments, the catheter 100 further comprises a guidewire 140 movable inside the first lumen 111.

In some embodiments, the diameter of the guidewire 140 ranges from about 0.20 mm to about 0.65 mm, such as about 0.30 mm to about 0.60 mm, or about 0.40 mm to about 0.50 mm.

In some embodiments, the catheter 110 further comprises a microcatheter and a stent-retriever inside the microcatheter (not shown in FIGS. 1-3) movable inside the first lumen 111.

Referring to FIG. 2, in some embodiments, the second opening 225 of the second tube 220 is reclined against a surface (for example, the surface of first tube 210 to which the second tube 220 integrally connects) of the first tube 210 such that the second opening 225 of the second tube 220 does not substantially hinder a movement of a guidewire or a stent-retriever inside the first lumen 211, such as when the guidewire or the stent-retriever is being retracted.

Referring to FIG. 2, in some embodiments, the angle of reclining between the second opening 225 of the second tube 220 and the surface (for example, the surface of first tube 210 to which the second tube 220 attaches) of the first tube 110 ranges from 0 to about 60 degrees, such as from 0 to about 55 degrees, from 0 to about 50 degrees, from 0 to about 45 degrees, from 0 to about 40 degrees, from 0 to about 35 degrees, from 0 to about 30 degrees, from 0 to about 25 degrees, from 0 to about 20 degrees, or from 0 to about 15 degrees.

Referring to FIG. 2, in some embodiments, a distal in-lumen portion 227 of the second tube distal to the second opening 215 of the first tube 210 is reclined against a surface of the first tube 210 such that the distal in-lumen portion 227 of the second tube 220 does not hinder the advancing movement of a guidewire or a stent-retriever to pass the distal in-lumen portion 227.

Referring to FIG. 2, in some embodiments, the angle of reclining between the distal in-lumen portion 227 of the second tube 220 and the surface (for example, the surface of first tube 210 to which the second tube 220 attaches) of the first tube 110 ranges from 0 to about 60 degrees, such as from 0 to about 55 degrees, from 0 to about 50 degrees, from 0 to about 45 degrees, from 0 to about 40 degrees, from 0 to about 35 degrees, from 0 to about 30 degrees, from 0 to about 25 degrees, from 0 to about 20 degrees, or from 0 to about 15 degrees.

Referring to FIG. 1, in some embodiments, the catheter 110 further comprises a syringe 150 connected to the first tube 110. In some embodiments, the syringe 150 connects to the first opening 113 (not shown in FIGS. 1-2). In some embodiments, the syringe 150 connects to the third opening 117.

In some embodiments, the syringe 150 is connected to the first tube 110 via a Luer-lock system.

Method of Removing Blood Clot

In some aspects, the present invention is directed to a method of removing a blood clot from a blood vessel of a subject.

In some embodiments, the subject is a vertebrate, such as a mammal, such as a human.

In some embodiments, the method uses a catheter the same as or similar to those described elsewhere herein, such as in the "Neuroaspiration Catheter" section.

In some embodiments, the method includes moving the wire inside the second lumen (e.g., wire 130 within lumen 121 shown in FIG. 1) the second lumen of the catheter in the blood vessel until the tip of the wire, makes contact, touches and/or passes through the blood clot; moving the first tube (e.g., 110) along the blood vessel using the wire (e.g., 130) as a guide and support until the second opening (e.g., 115) of the first tube is in proximity to the blood clot; applying a suction force to the first opening (e.g., 113) or the third opening (e.g. 117) of the first tube; (e.g., 110) and removing the first tube without removing the wire.

In some embodiments, the method further includes examining whether the blood clot is successfully removed. In some embodiments, whether the blood clot is successfully removed can be examined with a contrast dye injected into the blood vessel (e.g., using intravascular ultrasound).

In some embodiments, if the blood clot is not successfully removed, the first tube is navigated back to the site of the blood clot using the wire left in the blood vessel as a guide, and the aspiration is repeated.

In some embodiments, if the blood clot has not been sufficiently removed from the vessel, the method further includes using the rapid-exchange wire in place already as a guide to re-advance the first tube within the vessel until the first distal-end opening is in proximity to the blood clot. The method can further include using a stent-retriever inside a microcatheter through the first tube, advancing it through the clot beyond the first distal end-opening, then deploying the stent-retriever across the clot by withdrawing the microcatheter and subsequently removing the microcatheter. The method can further include removing the first and second tube as a unit along with the stent-retriever while applying the suction through the first proximal end opening of the first tube.

In some embodiments, each navigation attempt (including the first attempt) is aided by a guidewire (such as the guidewire 140 or 240 shown in FIG. 1 or 2) in addition to the wire.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

REFERENCE NUMBERS APPEARED IN THE FIGURES

Nueroaspiration catheter (also referred to as "aspiration catheter"): 100, 200 and 300;
First tube: 110, 210 and 310;
First lumen: 111, 211 and 311;
First opening of the first tube: 113, 213 and 313;
Second opening of the first tube: 115, 215 and 315;
Third opening of the first tube: 117, 217 and 317;
Second tube: 120, 220 and 330;
First opening of the second tube: 123, 223 and 323;
Second opening of the second tube: 125, 225 and 325;
Distal in-lumen portion of the second tube: 227
Wire: 130, 230 and 330;
Guide wire: 140, 240 and 340;
Syringe: 150, 250 and 350.

What is claimed is:

1. A dual-lumen neuroaspiration catheter comprising:
   a first tube having an outer wall, an inner wall, a first lumen defined by the space within the inner wall, a first proximal-end opening, and a first distal-end opening, wherein the first lumen is configured for advancing at least one of a guidewire, a microcatheter, and a stent-retriever device therein;
   a second tube having a second lumen, a second proximal-end opening, and a second distal-end opening, wherein the second proximal-end opening is proximal to the first distal-end opening, wherein the second distal-end opening is proximal to the first distal-end opening, and wherein the second tube is integrally formed with the first tube; and
   a rapid-exchange wire movable within the second lumen of the second tube;
   wherein the second distal-end opening is inside the first lumen.

2. The dual-lumen neuroaspiration catheter of claim 1, wherein the rapid-exchange wire is a microwire or a guidewire.

3. The dual-lumen neuroaspiration catheter of claim 1, wherein the first lumen has a first longitudinal axis, the second lumen has a second longitudinal axis, and the first longitudinal axis and the second longitudinal axis are substantially parallel.

4. The dual-lumen neuroaspiration catheter of claim 3, wherein the second tube is about 5 cm to about 40 cm in length; and wherein the second tube is located along a distal portion of the first tube, such that the second proximal-end opening is about 5 cm to about 40 cm from the first distal-end opening.

5. The dual-lumen neuroaspiration catheter of claim 1, wherein the second proximal-end opening is formed by a first sidewall opening in the first tube.

6. The dual-lumen neuroaspiration catheter of claim 1, wherein the first tube is coupled to an aspiration device via the first proximal-end opening or via a second sidewall opening in the first tube.

7. The dual-lumen neuroaspiration catheter of claim 1, wherein the diameter of the second lumen and the diameter of the rapid-exchange wire are substantially matched, such that the second proximal-end opening and the second distal-end opening are not substantially in fluid communication.

8. The dual-lumen neuroaspiration catheter of claim 1, wherein the diameter of the first lumen is at least about twice the diameter of the second lumen.

9. The dual-lumen neuroaspiration catheter of claim 1, wherein at least one of the first distal-end opening and the second distal-end opening is obliquely angled up to about 60 degrees proximally.

10. The dual-lumen neuroaspiration catheter of claim 1, wherein the rapid-exchange wire is configured to contact or pass through a thrombus within a blood vessel of a patient.

11. The dual-lumen neuroaspiration catheter of claim 1, where the rapid-exchange wire is configured to guide advancement of the first tube within a blood vessel of a patient.

12. The dual-lumen neuroaspiration catheter of claim 1, wherein the rapid-exchange wire is configured to remain in place within a blood vessel while the first tube and the second tube are removed from the blood vessel.

13. A method of removing a blood clot from a vessel using the dual-lumen neuroaspiration catheter of claim 1, the method comprising:
    advancing the rapid-exchange wire through the second lumen until a distal end of the rapid-exchange wire contacts or passes through the blood clot;
    using the rapid-exchange wire as a guide to advance the first tube within the vessel until the first distal-end opening is in proximity to the blood clot;
    aspirating the blood clot by applying suction force via the first proximal-end opening removing the first and second tubes of the dual-lumen neuroaspiration catheter while leaving the rapid-exchange wire in place.

14. The method of claim 13, further comprising:
    evaluating whether the blood clot has been sufficiently removed from the vessel; and
    if the blood clot has not been sufficiently removed from the vessel, using the rapid-exchange wire as a guide to re-advance the first tube within the vessel until the first distal-end opening is in proximity to the blood clot.

15. The method of claim 14, further comprising:
    re-aspirating the blood clot by applying suction force via the first proximal-end opening
    removing the first and second tubes of the dual-lumen neuroaspiration catheter while leaving the rapid-exchange wire in place; and
    re-evaluating whether the blood clot has been sufficiently removed from the vessel.

16. The method of claim 13, further comprising using at least one of a guidewire and a microcatheter within the first lumen as a guide to advance the first tube within the vessel.

17. The method of claim 13, wherein at least one of the evaluating and reevaluating steps is performed via intravascular ultrasound.

18. The dual-lumen neuroaspiration catheter of claim 1, wherein the first proximal-end opening and the first distal-end opening are substantially similar in diameter.

19. A dual-lumen neuroaspiration catheter comprising:
    a first tube having an outer wall, an inner wall, a first lumen defined by the space within the inner wall, a first proximal-end opening, and a first distal-end opening, wherein the first lumen is configured for advancing at least one of a guidewire, a microcatheter, and a stent-retriever device therein;
    a second tube having a second lumen, a second proximal-end opening, and a second distal-end opening, wherein the second proximal-end opening is proximal to the first distal-end opening, wherein the second distal-end opening is proximal to the first distal-end opening, and wherein the second tube is integrally formed with the first tube; and a rapid-exchange wire movable within the second lumen of the second tube;

wherein the second distal-end opening is inside the first lumen; and wherein at least one of the first distal-end opening and the second distal-end opening is obliquely angled up to about 60 degrees proximally.

20. A dual-lumen neuroaspiration catheter comprising:

a first tube having an outer wall, an inner wall, a first lumen defined by the space within the inner wall, a first proximal-end opening, and a first distal-end opening, wherein the first lumen is configured for advancing at least one of a guidewire, a microcatheter, and a stent-retriever device therein;

a second tube having a second lumen, a second proximal-end opening, and a second distal-end opening, wherein the second proximal-end opening is proximal to the first distal-end opening, wherein the second distal-end opening is proximal to the first distal-end opening, and wherein the second tube is integrally formed with the first tube; and a rapid-exchange wire movable within the second lumen of the second tube;

wherein the second distal-end opening is inside the first lumen; and wherein the first proximal-end opening and the first distal-end opening are substantially similar in diameter.

* * * * *